United States Patent
Rühe

(10) Patent No.: US 7,396,561 B2
(45) Date of Patent: Jul. 8, 2008

(54) SURFACE-ATTACHED POLYFUNCTIONAL POLYMER NETWORKS FOR SENSOR CHIPS

(75) Inventor: Jürgen Rühe, Eichstätten (DE)

(73) Assignee: Micronas Holding GmbH, Freiburg (DE)

( * ) Notice: Subject to any disclaimer, the term of this patent is extended or adjusted under 35 U.S.C. 154(b) by 390 days.

(21) Appl. No.: 10/343,035

(22) PCT Filed: Jul. 24, 2001

(86) PCT No.: PCT/EP01/08546

§ 371 (c)(1),
(2), (4) Date: Apr. 4, 2005

(87) PCT Pub. No.: WO02/10758

PCT Pub. Date: Feb. 7, 2002

(65) Prior Publication Data

US 2005/0202396 A1    Sep. 15, 2005

(30) Foreign Application Priority Data

Jul. 27, 2000  (EP)  ................... 00116340

(51) Int. Cl.
*B05D 3/04* (2006.01)
(52) U.S. Cl. .............. 427/214; 427/220; 427/221; 427/301; 427/302; 428/403; 428/406; 428/407
(58) Field of Classification Search .............. 427/214, 427/220, 221, 301, 302; 428/403, 406, 407
See application file for complete search history.

(56) References Cited

U.S. PATENT DOCUMENTS

| 4,352,884 | A | 10/1982 | Nakashima et al. |
|---|---|---|---|
| 5,026,785 | A | 6/1991 | Mage et al. |
| 5,478,893 | A | 12/1995 | Ghosh et al. |
| 5,695,925 | A | 12/1997 | Ebersole et al. |
| 5,854,169 | A * | 12/1998 | Heller et al. ............ 502/242 |
| 6,093,676 | A * | 7/2000 | Heller et al. ............ 502/242 |

FOREIGN PATENT DOCUMENTS

| EP | 0424833 | * | 5/1991 |
|---|---|---|---|
| EP | 1176423 B1 | | 2/2007 |
| FR | 2 682 609 A1 | | 4/1993 |
| WO | WO 98/32790 | | 7/1998 |
| WO | WO 00/43539 | | 7/2000 |

OTHER PUBLICATIONS

O Prucker, J. Ruhe: "Polymer Layers through Self-Assembled Monolayers of Initiators" Langmuir, vol. 14, No. 24, 1998, pp. 6893-6898.

O Prucker, J. Ruhe: "Synthesis of Poly(styrene) Monolayers Attached to High Surface Area Silica Gels through Self-Assembled Monolayers of Azo Initiators" Macromolecules, vol. 31, No. 3, 1998, pp. 592-601.

O Prucker, J. Ruhe: "Mechanism of Radical Chain Polymerizations Initiated by Azo Compounds Covalently Bound to the Surface of Spherical Particles" Macromolecules, vol. 31, No. 3, 1998, pp. 602-613.

European Search Report dated Feb. 1, 2001 for EP 00 11 6340.

* cited by examiner

*Primary Examiner*—Bernard Lipman
(74) *Attorney, Agent, or Firm*—Biotech Beach Law Group PC; Raymond Wagenknecht

(57) ABSTRACT

The invention relates to polyfunctional polymer networks comprising an assembly of cross-linked polymer subchains attached to a surface, with each polymer subchain comprising a multitude of identical or different repeating units carrying one or more functional groups which allows an interaction with a sample or probe molecule.

31 Claims, No Drawings

SURFACE-ATTACHED POLYFUNCTIONAL POLYMER NETWORKS FOR SENSOR CHIPS

Due to the steadily growing importance of microtechniques in a wide variety of scientific applications, the development of systems which allow the interaction of molecules with surfaces remains a critical issue. Such interactions include the possibility of removing specific molecules from a sample, e.g. to facilitate their analysis/detection, but also of presenting molecules on a surface, thus allowing subsequent reactions to take place. These principles for the immobilization of molecules can be applied in sensor or chromatographic systems or for the provision of modified surfaces in general.

In recent years there have been numerous approaches to fabricate sensor chips which are based on self-assembled monolayers (SAM's) of bifunctional molecules which directly or indirectly couple sample molecules to the sensor surface. Typically, these bifunctional molecules carry a silane or thiol/disulfide moiety in order to achieve a bond with the inorganic surface and an additional functional group (e.g. amino or epoxide groups) which interact with sample molecules, often contained in biological samples in the form of an oligonucleotide, a protein or a polysaccharide etc.

While the formation of a direct bond between the bifunctional compound and the sample molecule is possible, the sample molecules do not necessarily interact directly with the couplers forming the monolayer. Alternatively, appropriate immobilized biomolecules themselves can act as probes for the detection of sample molecules. Such probe molecules can equally be immobilized via a reaction with the free functional groups of the monolayer. In particular, if biomolecules are used as probe molecules, their presence may significantly enhance the specificity of the interaction of the sample molecules with the modified surface. For example, in cases where the fast analysis of a sample of DNA fragments or molecules is required, the monolayers of bifunctional molecules can first be brought in contact with synthetic oligonucleotides which will thus be immobilized. Subsequently, the hybridization of specific molecules, such as compatible strands from a sample is detected, e.g. via fluorescence microscopy, if dye-labeled sample molecules are used.

Although these techniques are well established for this purpose, the application of standard detection methods is problematic, especially in cases where the surface area available for the detection of one specific type of sample molecules is restricted, e.g. if a variety of molecules is to be analyzed in a parallel process, since the monolayers are limited in their graft density. For example, since the number of hybridized double strands per surface unit of a sensor can not easily be increased, suitable detectors have to meet very high requirements with regard to their sensitivity. Thus, the minimum surface area on a sensor necessary for the detection of one type of oligonucleotide can not be easily reduced. Moreover, the maximum density, i.e. one sample or probe molecule per functional group of the couplers can hardly be attained, since due to sterical hindrance on the two-dimensionally extended monolayer, only a fraction of the functional groups will be able to react with sample or probe molecules. Thus, the overall graft density is low and normally not well defined.

Similar problems with regard to the limited number of reaction sites per surface unit can arise in other applications, where it is desirable to immobilize an increased amount of molecules on a surface.

Various attempts have been made to overcome the problems outlined above. As regards the analysis of oligonucleotides, it has been tried to increase the graft density on the surface by using oligomers or polymers which carry an oligonucleotide strand (or a functional group for its attachment) together with a suitable group which allows the bonding of these oligomers or polymers to the surface of the sensor chip. Due to the increased flexibility of the oligomeric or polymeric chains, a larger fraction of the bifunctional oligomer or polymer molecules which are coupled to the surface is able to immobilize oligonucleotide probe molecules.

However, the total oligonucleotide graft density is not significantly increased, because the graft density of the bifunctional oligomeric or polymeric molecules on the surface is limited. This is a consequence of the fact that the self-assembly of the oligomers or polymers is hindered for kinetic reasons, because once the sensor surface is covered with such molecules, further polymers will have to diffuse against a concentration gradient in order to reach the surface.

A different approach to the above-mentioned self-assembled monolayers of bifunctional molecules for immobilization is using networks for DNA analysis. A disadvantage is that these networks are not coupled to the sensor surface and are not structured, i.e. do not form patterned arrays. Moreover, since the networks must be swellable in the used hybridisation medium there is a risc that the network is detached from the surface.

Accordingly, it is an object of the present invention to provide a surface which is modified with a polymer layer comprising functional groups for the interaction with sample or probe molecules, wherein the number of molecules interacting per surface unit is markedly increased compared to conventional monolayers of bifunctional molecules. In addition, the density of available interaction sites should be higher than that obtained from the reaction of bifunctional polymers or oligomers with the surface.

In the specific case of the detection of DNA molecules such as oligonucleotides, the object can be expressed as the provision of a surface with a graft density of synthetic oligonucleotide strands which is higher than that created by coupling the respective oligonucleotides to a functionalized monolayer of low molecular weight couplers. Also, the graft density should be higher then that resulting from the reaction of polymers or oligomers modified with a synthetic oligonucleotide single strand with the surface.

This object has been achieved by a surface to which a polyfunctional polymer network comprising an assembly of crosslinked polymer subchains (forming the "meshes" of the network) (hereinafter simply also referred to as "network") is covalently attached, which polymer subchains may each comprise a multitude of identical or different repeating units carrying one or more functional groups that allow an interaction, preferably a covalent interaction, of the polymer with sample or probe molecules. The number of "anchor groups" attaching or coupling the network to the surface determines the adhesion strength of the network to the surface and the mechanical strength of the entire system. The number of these anchoring points is (as will be explained below) controlled via the surface density of the used immobilized initiators. If, for example, such a polyfunctional polymer network is used to immobilize one or more synthetic oligonucleotide probes, complementary nucleic acids can subsequently be detected from a mixture of sample molecules after a hybridization reaction has taken place. Surprisingly, it has been found that such a surface-bound polyfunctional polymer network does not suffer from the problems of conventional detection methods where a high functional group density at the surface could not be achieved. Moreover, since the flexibility of the polyfunctional polymer network allows a complete coverage of the sensor surface, surface effects, e.g. during laser scanning, can be avoided. Further, the surface-bound polyfunctional networks are stable, may easily be structured, i.e. may form patterned arrays, and provide an improvement in sensitivity of the sensor.

The term "interaction", as used in this specification includes the formation of covalent bonds, as well as attractive ionic and van-der-Waal's forces and hydrogen bonds. The respective functional moiety within the polyfunctional polymer network or the probe molecules, which defines the type of interaction, will be selected according to the desired application of the surface according to the invention.

The expression "immobilize" is used hereinafter for an interaction of molecules with the polyfunctional polymer network resulting in the formation of a bond which is permanent under the chosen conditions. For example, probe molecules are immobilized by the polyfunctional network during their application on a sensor surface. However, by changing conditions (e.g. pH-value, addition of specific cleaving agents) an immobilization may sometimes be reversed.

The term "sample molecule" shall be used herein for molecules which are present in a sample and which couple temporarily or permanently to the polyfunctional network according to the invention. The present invention includes two general principles for an interaction of the inventive polyfunctional network with the sample molecules. In a first embodiment, the functional groups comprised within the polyfunctional network are chosen in order to allow a direct interaction of the chains with the sample molecules. In a second embodiment, probe molecules are immobilized at the functional groups of the polyfunctional network, and an interaction takes place between those probe molecules and the sample molecules.

Suitable probe molecules are molecules which are at least bifunctional, so that after their coupling to the polyfunctional polymer network new interaction sites are present in the surface-bound polyfunctional network according to the invention, which allow an interaction with sample molecules. Preferably, the probe molecules provide highly specific interaction sites for the sample molecules. They can be derived from natural or non-natural sources. Particularly preferred probe molecules are biomolecules such as nucleic acids, including DNA, RNA or PNA (peptide nucleic acid), most preferably oligonucleotides or aptamers, polysaccharides, proteins including glycosidically modified proteins or antibodies, enzymes, cytokines, chemokines, peptide hormones or antibiotics, and peptides. In order to ensure a sufficient stability, e.g. during a sensor application, the probe molecules are preferably covalently bound to the polyfunctional polymer network.

Depending on use, a multitude of identical probe molecules or a mixture of two or more different probes may be immobilized. For example, a set of identical probe molecules is preferred for the application of the polyfunctional polymer network as an affinity matrix.

The polyfunctional polymer network according to the present invention comprises an assembly of cross-linked polymer subchains which are attached to a surface. Preferably the bonds between the polyfunctional polymer network and the surface are covalent. The introduction of branched polymers is possible, if desired. In some cases addition of comonomers which allow a tayloring of the physical properties of the network depending on the desired application is appropriate.

The minimum components of the network are the functionalized repeating units and the cross-linking units. For the functionalized repeating units the subchains of the polymer network contain repeating units which carry at least one of the functional groups which can interact with sample or probe molecules. However, in order to impart certain advantageous properties to the polyfunctional polymer network, a copolymer, formed from these monomers with specific functional groups for the interaction with sample or probe molecules (hereinafter referred to as "functionalized monomers") together with other comonomers can be used.

For example, the reaction of the sample or probe molecules with the polyfunctional polymer network is significantly facilitated if the polyfunctional polymer network is swellable in the solvent containing these molecules, so that comonomers should preferably be chosen which show a strong interaction with the solvent in question. This can be achieved by using comonomers which improve the swellability of the network. Since, in a most preferred embodiment of the present invention, biomolecules, which are normally present in aqueous solutions, interact with the polyfunctional polymer network, said polyfunctional polymer network is preferably water-swellable. The water-swellability can be adjusted over a broad range by appropriate selection of suitable monomers, as long as the swellability does not lead to detachment of the polymer layer from the support and does not negatively affect the surface properties (i.e. evenness or constant thickness of surface coating) needed for fluorescent analyte detection.

Thus, for example, one or more comonomers can be used which are polar, or even soluble in water, if a homopolymer of functionalized monomers does not show sufficient interaction with water to allow a fast reaction of the molecules to be detected with the functional groups. Both types of monomers, functionalized as well as comonomers, preferably contain a C—C double bond which can react in a radical polymerization reaction. Examples for suitable comonomers which yield a water swellable polymer are acrylic acid, methacrylic acid and derivatives thereof, e.g. esters and amides of these acids with alcohols or amines preferably comprising 1 to 12 carbon atoms.

Common examples of this group of monomers are hydroxyethyl methacrylate, acrylamide and dimethyl acrylamide. Another suitable monomer is vinyl pyrrolidon. It is also possible to use monomers that yield at first water insoluble polymers which can then be transferred to water soluble derivatives. A suitable example for this group of polymers is polyvinyl alcohol which can be obtained, for example, by saponification of polyvinyl acetate.

If a copolymer is used, the ratio of comonomers to functionalized monomers is determined prior to the polymerization process in order to define the composition of the resulting polymer chains of the polyfunctional polymer network. Preferably, the ratio of the comonomers to the functionalized monomers ranges from 50/1 to 1/1, more preferably form 20/1 to 2/1.

The functional groups which are necessary to allow an interaction of the polyfunctional polymer network with the sample or probe molecules are preferably present in side chains of the polymer subchains of the polyfunctional polymer network. A "multitude" of functional groups comprised in polymer subchains of the polyfunctional polymer network of the present invention means at least two, but preferably more than two groups per polymer subchain. Since the concerned functional groups are preferably comprised in repeating units forming the polymer subchains of the polyfunctional polymer network, their number may amount up to several thousand, e.g. up to 10000 of these groups present in a single subchain, depending on the size of the probe or sample molecule to be immobilized. Preferably, each chain comprises 20 to 1000 of these functional groups.

Suitable functionalized repeating units which are present in the polymer subchains of the polyfunctional polymer network are those repeating units which comprise a polymerizable C—C double bond, as well as a further functional moiety that does not take part in the polymerization process. Preferably, this functional group is linked to the main polymer subchains of the polyfunctional polymer network via a $C_2$-$C_{10}$, more preferably a $C_3$-$C_7$ alkyl chain as a spacer.

The spacer molecules can be part of the functionalized monomers. Suitable monomers for this approach include acrylic and methacrylic esters or amides of $C_2$-$C_{10}$ alcohols or $C_2$-$C_{10}$ amines. In order to serve as spacers, these alcohols or amines carry an additional functional group at the terminal opposite to the one forming the ester or amide bond. This functional group either represents the one necessary for the interaction with the sample or probe molecules, or can be transformed to such a suitable functional group in a further step.

Alternatively, it is also possible to attach these spacer molecules to suitable reactive segments within the polymer subchains of the polyfunctional polymer network after its formation. In this case, reactive monomers have to be present during polymerization, such as acrylic or methacrylic acid chlorides or reactive esters thereof, as N-hydroxy succinimides or other monomers, e.g. maleic anhydride. These preferred reactive monomers can form covalent bonds to the bifunctional alcohols or amines that may be used as spacers.

The monomers carrying the spacer unit can readily be synthesized from the respective acrylic or methacrylic acid chloride or anhydride and the ω-amino or hydroxy carboxylic acid. The resulting product can be transformed to the active ester derivative by using e.g. N-hydroxy succinimide. A detailed procedure for the synthesis of several examples of such monomers can be found in the literature, e.g. in H.-G. Batz, J. Koldehoff, Macromol. Chem. 177 (1976) 683.

As outlined above, it is possible to use reactive monomers which directly yield the polymer subchains of the polyfunctional polymer network according to the invention. Alternatively, monomers can be chosen which carry a precursor of the functional group to be used on the final surface, e.g. an acid chloride or an acid anhydride. They can subsequently be transformed to reactive groups, e.g. NHS ester or glycidylester groups, which allow an interaction of the polyfunctional polymer network with sample or probe molecules under the desired conditions.

Thus, all polymerizable monomers are suitable for the purposes of the present invention, as long as they can be combined with, or comprise, functional groups necessary to allow an interaction of the polyfunctional polymer network with the sample molecules or probe molecules.

Functional groups which can be used for the purposes of the present invention are preferably chosen according to the molecules with which an interaction is to be achieved. The interaction can be directed to one single type of sample molecule, or to a variety of sample molecules. Since one important application of the present invention is the detection of specific molecules in biological samples, the functional groups present within the polyfunctional polymer network will preferably interact with natural or synthetic biomolecules which are capable of specifically interacting with the molecules in biological samples, leading to their detection. Suitable functional moieties will preferably be able to react with nucleic acids and derivatives thereof, such as DNA, RNA or PNA, e.g. oligonucleotides or aptamers, polysaccharides, proteins including glycosidically modified proteins or antibodies, enzymes, cytokines, chemokines, peptide hormones or antibiotics or peptides or labeled derivatives thereof.

Moreover, it will be possible to conduct the coupling reaction between the molecules to be detected or the synthetic oligonucleotides and the polyfunctional polymer network under conditions which are not detrimental to the sample or probe molecules. Consequently, in an nucleic acid sensor application, the reaction should be carried out in an aqueous solution, and the temperature should not be raised above 95° C.

Also, the coupling reaction should proceed at a reasonable rate so that the detection can preferably be accomplished within less than 24 hours without requiring extreme pH-values in the solution. For the immobilization of synthetic oligonucleotide single strands, the pH should range between 7 and 11, preferably 7 to 10. During the hybridization reaction of the nucleic acid sample molecules with the probe molecules, the bond between the functional group and the synthetic oligonucleotide single strand as well as the bonds of the polyfunctional polymer network to the substrate have to be able to withstand temperatures of more than 65° C., and a pH of 6-9. In cases where DNA is used as a sample molecule, the temperatures may have to be raised up to about 95° C. in order to effect a separation of the DNA strands, which is necessary for hybridization.

Since most of the probe molecules, especially in biological or medical applications, comprise sterically unhindered nucleophilic moieties, preferred interactions with the polyfunctional polymer network comprise nucleophilic substitution or addition reactions leading to a covalent bond between the polymer subchains and the sample or probe molecules. For example, synthetical oligonucleotides are usually provided with a free amine group at one end (5' or 3'). Thus, exemplary functional groups provide, for example, a reactive double bond, an equivalent for a double bond (as e.g. an epoxy group) or a reactive leaving group. However, ionic or vander-Waals forces as well as hydrogen bonds can also be used to couple sample molecules to the polyfunctional polymer network if the functional groups are chosen accordingly.

Preferred functional groups can be chosen from prior literature with respect to the classes of molecules which are to be immobilized and according to the other requirements (reaction time, temperature, pH value) as described above. A general list can for example be found in the text book "Bioconjugate Techniques" by G. T. Hermanson, Academic Press, 1996. In the case of the attachment of amino-terminated oligonucleotides, examples for suitable groups are so-called active or reactive esters as N-hydroxy succinimides (NHS-esters), epoxides, preferably glycidyl derivatives, isothiocyanates, isocyanates, azides, carboxylic acid groups or maleinimides.

As preferred functional monomers which directly result in polyfunctional polymer subchains of the polyfunctional polymer network, the following compounds can be employed for the purposes of the present invention:
  acrylic or methacrylic acid N-hydroxysuccinimides,
  N-methacryloyl-6-aminopropanoic acid hydroxysuccinimide ester,
  N-methacryloyl-6-aminocapronic acid hydroxysuccinimide ester or
  acrylic or methacryl acid glycidyl esters.

Depending on the application, there is the possibility of providing the polymer subchains of the polyfunctional polymer network with a combination of two or more different functional groups, e.g. by carrying out the polymerization leading to the polymer subchains in the presence of different types of functionalized monomers. Alternatively, the functional groups may be identical.

An advantageous and preferred method for the preparation of the polyfunctional polymer network according to the invention is described in the following:

In a first step, a surface is covalently covered by a monolayer of polymerization initiators or starter molecules. The groups in these initiators which allow the initiation of the polymerization are usually chosen e.g. from peroxo groups or azo groups if a thermally initiated radical mechanism is to be used. Aromatic ketones such as benzoin, benzil or benzophenone derivatives are preferably used if the polymers are formed by photochemical initiation. Aromatic ketones comprising sulphur may equally be used, if desired, in order to shift the suitable wavelength for photoinitation to a longer wavelength region. In addition to such labile groups, suitable initiators for the preferred process according to the invention carry one or more groups suitable for their attachment to the surface to be covered by the polymer subchains of the polyfunctional polymer network. The same or different initiators may also be present in the polymerization mixture.

The polymer subchains of the polyfunctional polymer network according to the present invention are usually grown from the surface via a chain reaction and are cross-linked simultaneously (cross-linking polymerization using in part immobilized initiators). While radical mechanisms are preferred for practical reasons, the application of ionic or other polymerization techniques is also possible.

due to their increased stability on surfaces. Moreover, the present invention is not restricted to inorganic surfaces. Organic polymer surfaces can also be used as substrates to carry the polyfunctional polymer network, and there is also the possibility to include the starters for the polymerization reaction directly into such a surface forming polymer. Thus, suitable surfaces according to the present invention are preferably selected from non-porous materials such as e.g. microscope slides, polished silicon wafers, polymer plates, vials and wells.

Preferred examples for initiators which can be used for the purposes of the present invention are listed below, together with their structure formulae:

4,4'-Azobis-(4-cyano pentanoic acid (3'-chlorodimethylsilyl) propyl ester), compound 1 or the respective di- and trichloro or mono-, di- and trialkoxy silane analogs, 2,4'-Azo-(4-cyano pentanoic acid (3''-chlorodimethylsilyl) propyl ester), compound 2 or the respective di- and trichloro or mono-, di- and trialkoxy silane analogs; or the respective compounds with an undecyl spacer rather than an propyl spacer, or disulfide or thiol derivatives of this general type of azo compounds, 4-(3'-chlorodimethylsilyl)propyloxy) benzophenone, compound 3 or the respective di- and trichloro- or mono-, di- and trialkoxy silane analogs, silane and disulfide/thiol derivatives of arylazomalodinitriles, such as compound 4.

| compound number | structure |
|---|---|
| 1 | Cl—Si(Me)(Me)—CH₂CH₂CH₂—O—C(=O)—CH₂CH₂—C(CN)(Me)—N=N—C(Me)(CN)—CH₂CH₂—C(=O)—O—CH₂CH₂CH₂—Si(Me)(Me)—Cl |
| 2 | Cl—Si(Me)(Me)—CH₂CH₂CH₂—O—C(=O)—CH₂CH₂—C(Me)(CN)—N=N—C(Me)(Me)(CN) |
| 3 | Cl—Si(Me)(Me)—CH₂CH₂CH₂—O—C₆H₄—C(=O)—C₆H₅ |
| 4 | Cl—Si(Me)(Me)—CH₂CH₂—C₆H₄—N=N—C(Me)(CN)(CN) |

The functional groups comprised in the initiator molecules for surface attachment have to be adapted to the sensor surface used. For the preparation of the initiator monolayer on metal oxides, especially silicon oxide surfaces (evaporated or sputtered $SiO_x$ layers, $SiO_2$ surfaces of silicon wafers, glass, quartz), chlorosilane moieties or alkoxysilanes are used. Thiol or disulfide groups can be employed for the modification of gold surfaces. However, silanes are usually preferred Preferred examples for suitable cross-linkers are: bisacrylates, bismethacrylates, for example oligo-ethylene glycol bismethacrylates such as ethylene glycol bismethacrylate, and bisacrylamides, for example ethylene diamine bisacrylamide.

Upon initiation of the polymerization reaction, preferably by a heating step (thermal initiation) or exposure to radiation (photoinitiation) in the presence of polymerizable functionalized monomers and cross-linkers, polymer subchains can be grown from the surface and are simultaneously cross-linked. The polymerization can be carried out under standard reaction conditions known in the art. If this technique is applied, the graft densities of the resulting polyfunctional polymer network can be controlled over a wide range, for example by variation of the polymerization time. Moreover, graft densities can be achieved that are inaccessible by other methods. Thus, the polymer subchains of the polyfunctional polymer network can be attached such that the average distance between anchoring sites on the surface is 5 nm or less, e.g. 2 to 5 nm. Advantageously, such graft densities can be achieved independent of the molecular weight of the attached chains, e.g. even for molecular weights of 100000 g/mol or more.

Furthermore, the preferred in-situ formation of a polyfunctional polymer network on a surface according to the present invention allows the control of the average molecular weight of the attached polymer subchains of the polyfunctional polymer network independent of the graft density.

According to this precise control of the parameters graft density, cross-link density and molecular weight, it is possible to adapt the properties of the respective polyfunctional polymer network to a variety of applications. By adjusting the reaction conditions networks with thicknesses ranging from a few nanometers up to some milimeters or even more may be prepared. It is also possible to fine-tune the properties of the resulting polyfunctional polymer network, e.g. with respect to the accessibility of the functional groups for subsequently coupled probe and sample molecules which may vary considerably in their size and structure.

The polyfunctional polymer networks obtained via the above preferred method retain a fragment of the initiator in their structure which immobilizes them on the surface, namely the portion starting with the anchoring site and leading to the predetermined point of initiation as it is known in the art for all types of initiators, in particular those mentioned in this application.

Detailed information on the synthesis of initiator molecules, their reaction with surfaces and the preferred conditions of polymerization are described in:

O. Prucker, J. Rühe, Macromolecules, 1998, 31, 592;
O. Prucker, J. Rühe, Macromolecules, 1998, 31, 602 and
O. Prucker, J. Rühe, Langmuir, 1998, 24 (14), 6893.

Care should be taken to remove unreacted monomers as well as non-bonded or cross-linked polymer chains with suitable solvents after polymerization.

According to an alternative method, in a first step a polyfunctional polymer network may be pre-formed which is then covalently bound to a surface. A further alternative method comprises synthesizing long polymer chains with appropriate functional groups starting from immobilized (surface-bound) initiators (so-called "polymer brushes") followed by crosslinking the latter.

Polyfunctional polymer networks prepared according to the above methods can be applied to a wide variety of surfaces, independent of their shape. Even surfaces which are inaccessible for conventional surface modification methods can be provided with the polyfunctional polymer network according to the invention, since no bulky polymer molecules have to diffuse towards the surface.

Also, it is possible to create patterned arrays of the polyfunctional polymer network by various means. One way are standard photolithographic processes that can either be applied after polymerization (photoablation of the polymers through masks) prior to this step (photodecomposition or photoablation of the initiator monolayer masks) or during the polymerization by means of photopolymerization through masks. Other possible techniques for the creation of patterned polyfunctional polymer networks are microcontact printing or related methods, which may be applied during formation of the initiator layer or during polymerization. Finally, ink jet techniques or other microplotting methods can be used to create patterned initiator monolayers which can subsequently be transferred to patterned polyfunctional polymer network. Using any of these techniques, surface structures with dimensions in the micrometer range can be created. The high parallel mode of signal generation and a significant improvement in the integration of analytical data is the most promising feature of such techniques, which accordingly allow the optimization of automatic analytical procedures.

For the detection of a successful immobilization of sample or probe molecules on a polyfunctional polymer network, a variety of techniques can be applied. In particular, it has been found that the polyfunctional polymer networks of the present invention undergo a significant increase in their thickness which can be detected with suitable methods, e.g. ellipsometry. Mass sensitive methods may also be applied.

If nucleic acids, for example oligonucleotides with a desired nucleotide sequence or DNA molecules in a biological sample, are to be analyzed, synthetic oligonucleotide single strands can be reacted with the polyfunctional polymer network. The reaction is carried out under high humidity, preferably in a buffered aqueous solution. The reaction temperature can be raised above room temperature, as long as it is not detrimental to the oligonucleotides. Preferred temperatures are in the range of 40-60° C. In this application, a multitude of identical synthetic oligonucleotide strands or a mixture of different strands can be used. If different strands are used, their sequences should preferably be known.

Before the thus prepared surface is used in a hybridization reaction, unreacted functional groups are deactivated via addition of suitable nucleophiles, preferably $C_1$-$C_4$ amines, such as simple primary alkylamines (e.g. propyl or butyl amine), secondary amines (diethylamine) or amino acids (glycin).

Upon exposure to a mixture of oligonucleotide single strands, e.g. as obtained from PCR, which are labled, only those surface areas which provide synthetic strands as probes complementary to the PCR product will show a detectable signal upon scanning due to hybridization. In order to facilitate the parallel detection of different oligonucleotide sequences, printing techniques can be used which allow the separation of the sensor surface into areas where different types of synthetic oligonucleotide probes are presented to the test solution.

The term "hybridization" as used in accordance with the present invention may relate to stringent or non-stringent conditions. If not further specified, the conditions are preferably non-stringent. Said hybridization conditions may be established according to conventional protocols described, for example, in Sambrook, "Molecular Cloning, A Laboratory Manual", Cold Spring Harbor Laboratory, N.Y. (1989), Ausubel, "Current Protocols in Molecular Biology", Green Publishing Associates and Wiley Interscience, N.Y. (1989), or Higgins and Hames (Eds) "Nucleic acid hybridization, a practical approach" IRL Press Oxford, Washington D.C., (1985). The setting of conditions is well within the skill of the artisan and to be determined according to protocols described in the art. Thus, the detection of only specifically hybridizing sequences will usually require stringent hybridization and washing conditions such as for example 0.1×SSC, 0.1% SDS at 65° C. Exemplary non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions.

The nucleic acids to be analyzed may originate from a DNA library or a genomic library, including synthetic and semisynthetic nucleic acid libraries. Preferably, the nucleic acid library comprises oligonucleotides.

In order to facilitate their detection in an immobilized state, the nucleic acid molecules should preferably be labeled. Suitable labels include radioactive, fluorescent, phosphorescent, bioluminescent or chemoluminescent labels, an enzyme, an antibody or a functional fragment or functional derivative thereof, biotin, avidin or streptavidin.

Antibodies may include, but are not limited to, polyclonal, monoclonal, chimeric or single-chain antibodies or functional fragments or derivatives of such antibodies.

The general methodology for producing antibodies is well-known and has been described in, for example, Köhler and Milstein, Nature 256 (1975), 494 and reviewed in J. G. R. Hurrel, ed., "Monoclonal Hybridoma Antibodies: Techniques and Applications", CRC Press Inc., Boco Raron, Fla. (1982). Also the method taught by L. T. Mimms et al., Virology 176 (1990), 604-619, is applicable. As stated above, in accordance with the present invention the term "antibody" relates to monoclonal or polyclonal antibodies. Functional antibody fragments or derivatives provide the same specificity as the original antibody and comprise F(ab')$_2$, Fab, Fv or scFv fragments; see, for example, Harlow and Lane, "Antibodies, A Laboratory Manual", CSH Press 1988, Cold Spring Harbor, N.Y. Preferably the antibody of the invention is a monoclonal antibody. Furthermore, in accordance with the present invention, the derivatives can be produced by peptidomimetics. Such production methods are well known in the art and can be applied by the person skilled in the art without further ado.

Depending on the labeling method applied, the detection can be effected by methods known in the art, e.g. via laser scanning or use of CCD cameras.

Also comprised by the present invention are methods where detection is indirectly effected. An example of such an indirect detection is the use of a secondary labeled antibody directed to a first compound such as an antibody which binds to the biological molecule (sample molecule) of interest.

A further application of the polyfunctional polymer networks according to the invention lies in the field of affinity chromatography, e.g. for the purification of substances. For this purpose, polyfunctional polymer networks with identical functional groups or probe molecules are preferably used, which are contacted with a sample. After the desired substance has been immobilized by the polyfunctional polymer network, unbound material can be removed, e.g. in a washing step. With suitable eluents, the purified substance can then be separated from the affinity matrix.

Preferred substances which may be immobilized on such a matrix are nucleic acid molecules, peptides or polypeptides (or complexes thereof), such as antibodies, functional fragments or derivatives thereof, saccharides or polysaccharides.

A regeneration of the surfaces after the immobilization has taken place is possible, but single uses are preferred in order to ensure the quality of results.

With the polyfunctional polymer networks of the present invention, different types of samples can be analyzed with an increased precision and/or reduced need of space in serial as well as parallel detection methods. The sensor surfaces to which the polyfunctional polymer networks according to the invention are attached can therefore serve in diagnostic instruments or other medical applications, e.g. for the detection of components in physiological fluids, such as blood, serum, sputum etc.

Surfaces with the polyfunctional polymer networks according to the present invention can also immobilize starter molecules for synthetic applications in particular in solid phase synthesis, e.g. during the in situ formation of oligo- or polymers. Preferably, the oligo- or polymers are biomolecules and comprise peptides, proteins, oligo- or polysaccharides or oligo- or polynucleic acids. As immobilized initiators, a monomer of these macromolecules can be used.

Moreover, the polyfunctional polymer networks of the present invention can be used as gels in the separation of molecules, preferably biomolecules in an electrical field.

Generally, the present invention allows the provision of surfaces homogenically modified with polyfunctional polymer networks having superior surface adhesive properties and improved mechanical strength. Moreover, structured surfaces can be provided, e.g. by starting the polymerization from patterned arrays of initiator molecules. As a consequence, the polyfunctional polymer network can be adjusted optimally to the respective applications.

The disclosure content of the documents cited throughout the specification are herewith incorporated by reference.

The embodiments of the present invention are further illustrated in the following items:

A preferred process for the detection of sample nucleic acid molecules, preferably of single stranded nucleic acid molecules, using a polyfunctional polymer network according to the invention comprises the steps of:

providing a surface covalently covered with a polyfunctional polymer network according to the invention, immobilizing suitable probe molecules, preferably oligonucleotide single strands, on the polyfunctional polymer network via a reaction with the functional groups present in the polyfunctional polymer network, allowing a hybridization reaction to take place between the oligonucleotide single strands and the sample nucleic acid molecules, removing the non-hybridized nucleic acid molecules in a washing step, and detecting the hybridized nucleic acid molecules, preferably fluorometrically.

A preferred process for purifying a compound from a sample, using a polyfunctional polymer network according to the invention comprises the steps of:

providing a surface modified with a polyfunctional polymer network according to the invention, immobilizing a multitude of identical probe molecules on the polyfunctional polymer network, contacting the sample with the resulting polymer network, under conditions that allow binding of said compound to the probe molecules, and removing material from the sample that has not bound to the probe molecules.

This process may further include the step of separating the compound from the probe molecules by use of a suitable eluent.

The following examples illustrate the invention:

Synthesis of the Initiator

As an example, the preparation of compound 1 is described. The reaction pathway is illustrated below. The indices i-iii in the figure refer to the description of the various steps in the text.

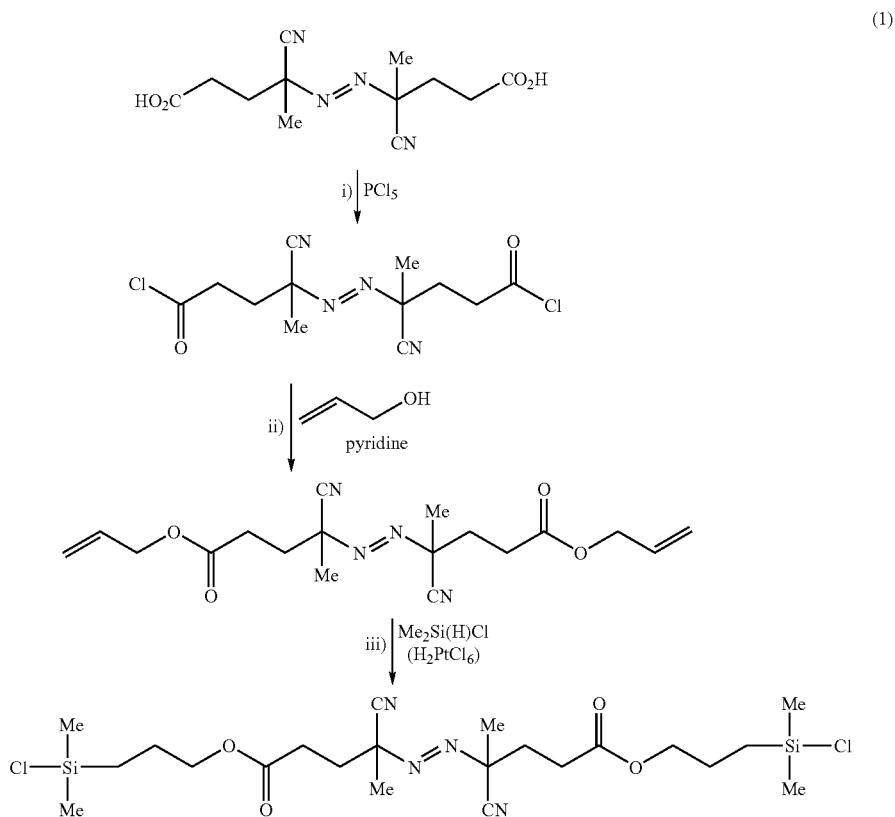

(1)

i) To a suspension of 40 g phosphorus pentachloride (PCl$_5$) in 50 ml methylene chloride cooled with an ice-bath was added dropwise a suspension of 10 g of 4,4'-azobis-(4-cyano pentanoic acid) in 50 ml methylene chloride. The mixture was allowed to warm to room temperature and was stirred overnight. The excess PCl$_5$ was filtered off and the remaining solution was concentrated until no more PCl$_5$ separated. The mixture was filtered again and the filtrate was added to 300 ml of cold hexane, causing the separation of the acid chloride as a white solid (yield: 90%).

ii) To a solution of 2.7 ml of allyl alcohol and 6.5 ml of pyridine in 50 ml methylene chloride at 0° C. was added dropwise a solution of 10 g of the acid chloride in 50 ml methylene chloride. The mixture was allowed to warm to room temperature and was stirred overnight. Then the solution was washed twice with 2N H$_2$SO$_4$, aqueous NaHCO$_3$ and water. The organic layer was dried over Na$_2$SO$_4$ and the solvent was evaporated. The resulting bis allylic ester was recrystallized from methanol (yield: 90%).

iii) To a suspension of 3 g of the bis allylic ester in 30 ml dimethyl chloro silane was added a solution of 30 mg of hexachloroplatinic acid in 0.5 ml of dimethyl ether/ethanol (1/1 v/v) and the mixture was heated to reflux for 3 h. The excess of the silane was evaporated yielding compound 1 as a pale green oil in quantitative yields. Residual platinum catalyst was removed by filtration of a methylene chloride solution of the product over anhydrous Na$_2$SO$_4$.

Formation of an Initiator Monolayer

The initiator synthesized under (1) was immobilized at room temperature on a glass surface under inert conditions (atmosphere of dry nitrogen) using anhydrous toluene as a solvent and dry triethylamine as a catalyst. The toluene solution shows a concentration of the initiator of about 50 mmol/l and triethylamine is added up to a concentration of about 10 mmol/l. The samples were kept in the solution overnight and then cleaned by extensive rinsing with methanol and chloroform.

Synthesis of the Functionalized Monomer

As an example, the synthesis of N-methacryloyl-6-aminocapronic acid hydroxysuccinimide ester is described. The reaction pathway is shown below. The indices i-iii in this figure refer to the description of the various steps in the text.

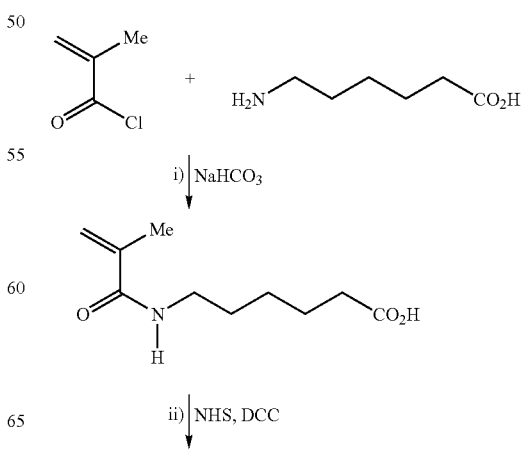

-continued

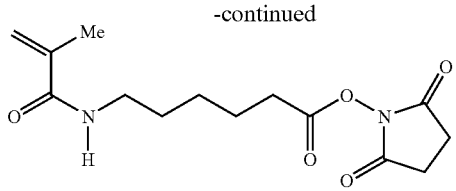

i) A solution of 13.2 g 6-aminocaproic acid and 20 g NaHCO$_3$ in 100 ml water and 50 ml 1,4-dioxane was slowly added to a solution of 10.3 ml of methacrylic acid chloride in 50 ml 1,4-dioxane. The solution was stirred overnight. Then 50 ml of water were added and the mixture was washed three times with 100 ml portions of ethyl acetate. The water layer was acidified (pH 2) with dilute hydrochloric acid and then extracted with three 100 ml portions of ethyl acetate. The combined organic layers were dried over Na$_2$SO$_4$, concentrated to a volume of about 50 ml and added to 350 ml of cold hexane.

This mixture was cooled to −20° C. and the product slowly separated overnight as white crystals (yield: ca. 14 g).

ii) A solution of 14 g of the acid in 300 ml methylene chloride was cooled to 5° C. and 8.2 g of N-hydroxy succinimide (NHS) and 14.6 g of N,N-dicyclohexyl carbodiimide were added. The mixture was kept at 5° C. overnight. The precipitate (dicyclohexylurea) was filtered off and the solvent was evaporated. During this step, additional urea separated in some cases and was also filtered off. The crude product was recrystallized from isopropanol to yield about 15 g of the NHS ester monomer.

Formation of a Polyfunctional Polymer Network

A solution comprising the following ingredients was used:
40 mole % N,N-dimethyl acrylamide (for the water-swellable basis polymer),
10 mole % N-methacryloyl-6-aminocapronic acid hydroxysuccinimide ester (for the functionalized repeating units),
5 mole % ethylene glycol bismethacrylate (for the cross-linking units),
1 mole % azobisisobutyronitril (as an initiator),
balance (to 100 mole %) ethanol.

This solution was given into a mould and said mould pressed firmly onto a initiator-modified substrate (with immobilized initiator). After heating to 70° C. polymerization was performed for 10 hours. Thereafter, the mould was removed and the resultant surface-attached network washed with ethanol.

Detection of Oligonucleotides Strands

The obtained surface was exposed to 1 nl of a 10 μM oligonucleotide-solution and the coupling reaction was allowed to proceed at about 40-50° C. for two hours in an aqueous solution.

The synthetic oligonucleotide was 5-amino modified and the solution was buffered with a 100 mM sodium phosphate buffer at a pH of 8.0. After the coupling reaction, the sensor surface was rinsed with the sodium phosphate buffer. In order to define the spatial extension of the specific types of oligonucleotide on the sensor surface for parallel detection, the reactant was printed onto the polyfunctional polymer network.

The surface thus prepared was allowed to react with a Cy5 labeled PCR product in a buffer of 2×SSC, 10% dextrane sulphate and 50% formamide for 12 h at 28° C. The DNA content was 100 ng DNA/80 μl sample. After the hybridization reaction has taken place, the surface was washed in SSC-buffer and the result was detected fluorometrically via laser activation with a CCD camera. A fluorescence signal could only be detected for those areas which carried synthetic oligonucleotides complementary with the PCR product.

The invention claimed is:

1. Process for the formation of a polyfunctional polymer network covalently attached to a sensor surface, wherein said network comprises cross linked polymer subchains having a multitude of identical or different repeating units carrying one or more functional groups which allow an interaction of the polymer with sample or probe molecules, the process comprising the steps of:
   (a) covering the sensor surface with a monolayer of a polymerization initiator which comprises one or more functional groups suitable for covalent attachment to the surface;
   (b) contacting the polymerization initiator monolayer with a solution comprising polymerization initiators, cross-linkers, and a polymerizable mixture of monomers and comonomers carrying functional groups which allow an interaction with sample or probe molecules;
   wherein said contacting is followed by simultaneously initiating and carrying out a crosslinking polymerization reaction both in solution and on the sensor surface.

2. Process for the formation of a polyfunctional polymer network covalently attached to a sensor surface, wherein said network comprises cross-linked polymer subchains having a multitude of identical or different repeating units carrying one or more functional groups which allow an interaction of the polymer with sample or probe molecules, the process comprising the steps of:
   (a) covering the sensor surface with a monolayer of a polymerization initiator which comprises one or more functional groups suitable for covalent attachment to the surface, wherein said initiator comprises a chlorosilane, a disulphide, or a thiol group;
   (b) contacting the polymerization initiator monolayer with a polyfunctional polymer network comprising cross linked polymer subchains, obtained by polymerization of monomers and comonomers carrying functional groups which allow an interaction with sample or probe molecules, in the presence of cross-linkers,
   wherein said contacting is followed by initiating a covalent binding reaction between the polymer network and the sensor surface-attached polymerization initiators.

3. Process according to claim 1, wherein said initiator comprises a chlorosilane, an alkoxysilane, a disulphide, or a thiol group.

4. Process according to claim 1, wherein said initiator comprises a group chosen from azo groups, peroxo groups, or a ketone group in conjunction with an aromatic system.

5. Process according to claim 2, wherein said initiator comprises a group chosen from azo groups, peroxo groups, or a ketone group in conjunction with an aromatic system.

6. Process according to claim 4, wherein said initiator comprises a group chosen from aromatic ketones or aromatic ketones containing sulphur.

7. Process according to claim 5, wherein said initiator comprises a group chosen from aromatic ketones or aromatic ketones containing sulphur.

8. Process according to claim 1, wherein said cross-linker is selected from the group consisting of bisacrylates, bismethacrylates and bisacrylamides.

9. Process according to claim 2, wherein said cross-linker is selected from the group consisting of bisacrylates, bismethacrylates and bisacrylamides.

10. Process according to claim 1, wherein said one or more functional groups are selected from the group consisting of carboxylic acids, maleinimides, N-hydroxy succinimides, epoxides, isothiocyanates, isocyanates, and azides.

11. Process according to claim 2, wherein said one or more functional groups are selected from the group consisting of carboxylic acids, maleinimides, N-hydroxy succinimides, epoxides, isothiocyanates, isocyanates, and azides.

12. Sensor surface having covalently attached thereto a polyfunctional polymer network comprising cross-linked polymer subchains having a multitude of identical or different repeating units carrying one or more functional groups which allow an interaction of the polymer with sample or probe molecules, obtained by a process comprising the steps of:
    (a) covering the sensor surface with a monolayer of a polymerization initiator which comprises one or more functional groups suitable for covalent attachment to the surface;
    (b) contacting the polymerization initiator monolayer with a solution comprising polymerization initiators, cross-linkers, and a polymerizable mixture of monomers and comonomers carrying functional groups which allow on interaction with sample or probe molecules;
    wherein said contacting is followed by simultaneously initiating and carrying out a crosslinking polymerization reaction both in solution and on the sensor surface.

13. Sensor surface having covalently attached thereto a polyfunctional polymer network comprising cross-linked polymer subchains having a multitude of identical or different repeating units carrying one or more functional groups which allow an interaction of the polymer with sample or probe molecules, obtained by a process comprising the steps of:
    (a) covering the sensor surface with a monolayer of a polymerization initiator which comprises one or more functional groups suitable for covalent attachment to the surface, wherein said initiator comprises a chlorosilane, a disulphide, or a thiol group;
    (b) contacting the polymerization initiator monolayer with a polyfunctional polymer network comprising cross linked polymer subchains, obtained by polymerization of monomers and comonomers carrying functional groups which allow an interaction with sample or probe molecules, in the presence of cross- linkers;
    wherein said contacting is followed by initiating a covalent binding reaction between the polymer network and the sensor surface-attached polymerization initiators.

14. Sensor surface according to claim 12, wherein said one or more functional groups are selected from the group consisting of carboxylic acids, maleinimides, N hydroxy succinimides, epoxides, isothiocyanates, isocyanates, and azides.

15. Sensor surface according to claim 13, wherein said one or more functional groups are selected from the group consisting of carboxylic acids, maleinimides, N hydroxy succinimides, epoxides, isothiocyanates, isocyanates, and azides.

16. Sensor surface according to claim 12, further comprising a multitude of different probe molecules immobilized at said polymer subchains via a reaction with said functional groups, wherein said probe molecules are selected from the group consisting of proteins, peptides, polysaccharides, nucleic acids, PNAs, and derivatives thereof.

17. Sensor surface according to claim 13, further comprising a multitude of different probe molecules immobilized at said polymer subchains via a reaction with said functional groups, wherein said probe molecules are selected from the group consisting of proteins, peptides, polysaccharides, nucleic acids, PNAs, and derivatives thereof.

18. Sensor surface according to claim 12, wherein said polymer subchains comprise segments that make said polymer network water-swellable.

19. Sensor surface according to claim 13, wherein said polymer subchains comprise segments that make said polymer network water-swellable.

20. Sensor surface according to claim 18, wherein said water swellability is provided by monomers chosen from acrylic acid, methacrylic acid, dimethyl acrylamide or vinyl pyrrolidon.

21. Sensor surface according to claim 19, wherein said water swellability is provided by monomers chosen from acrylic acid, methacrylic acid, dimethyl acrylamide or vinyl pyrrolidon.

22. Sensor surface according to claim 12, wherein said polyfunctional polymer network forms a patterned array on said surface.

23. Sensor surface according to claim 13, wherein said polyfunctional polymer network forms a patterned array on said surface.

24. A method of using a sensor surface for detecting sample nucleic acid molecules, which comprises the steps of:
    (a) providing a sensor surface according to claim 16;
    (b) allowing a hybridization reaction to take place between the probe and the sample; followed by
    (c) removal of the non hybridized nucleic acid molecules in a washing step; and
    (d) detection of the hybridized nucleic acid molecules.

25. A method of using a sensor surface for detecting sample nucleic acid molecules, which comprises the steps of:
    (a) providing a sensor surface according to claim 17;
    (b) allowing a hybridization reaction to take place between the probe and the sample; followed by
    (c) removal of the non hybridized nucleic acid molecules in a washing step; and
    (d) detection of the hybridized nucleic acid molecules.

26. Medical or diagnostic instrument, comprising a surface according to claim 12.

27. Medical or diagnostic instrument, comprising a surface according to claim 13.

28. A method of using a surface for the immobilization of starter molecules for the formation of oligomers or polymers, the method comprising the steps of:
    (a) providing a surface according to claim 12; and
    (b) immobilizing starter molecules for the formation of oligomers or polymers.

29. The method according to claim 28, wherein the oligomers or polymers formed are suitable for nucleic acid or peptide synthesis.

30. A method of using a surface for the immobilization of starter molecules for the formation of oligomers or polymers, the method comprising the steps of:
    (a) providing a surface according to claim 13; and
    (b) immobilizing starter molecules for the formation of oligomers or polymers.

31. The method according to claim 30, wherein the oligomers or polymers formed are suitable for nucleic acid or peptide synthesis.

* * * * *